US011629302B2

(12) United States Patent
Kaita et al.

(10) Patent No.: US 11,629,302 B2
(45) Date of Patent: Apr. 18, 2023

(54) FUEL PRODUCTION PLANT

(71) Applicant: TOYOTA JIDOSHA KABUSHIKI KAISHA, Toyota (JP)

(72) Inventors: Keiji Kaita, Miyoshi (JP); Takahiko Hirasawa, Toyota (JP); Noriko Yasutani, Nagoya (JP); Hideo Kato, Nagoya (JP); Oji Kuno, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 17/850,125

(22) Filed: Jun. 27, 2022

(65) Prior Publication Data

US 2023/0034991 A1  Feb. 2, 2023

(30) Foreign Application Priority Data

Jul. 29, 2021  (JP) .............................. JP2021-124130

(51) Int. Cl.
*C10L 1/04* (2006.01)
*C25B 1/04* (2021.01)
(Continued)

(52) U.S. Cl.
CPC ................. *C10L 1/04* (2013.01); *C07C 1/12* (2013.01); *C12P 7/06* (2013.01); *C25B 1/04* (2013.01);
(Continued)

(58) Field of Classification Search
CPC ................ C10L 1/04; C10L 1100/0461; C10L 2290/26; C10L 2290/58; C07C 1/12; C12P 7/06; C25B 1/04
See application file for complete search history.

(56) References Cited

U.S. PATENT DOCUMENTS

2010/0280135 A1* 11/2010 Doty .................... C01B 3/36
518/703
2011/0009499 A1*  1/2011 Lutz ..................... C01B 3/34
204/278
(Continued)

FOREIGN PATENT DOCUMENTS

JP  2013-202044 A  10/2013
JP  2021-102532 A  7/2021

*Primary Examiner* — Ali Z Fadhel
(74) *Attorney, Agent, or Firm* — Oliff PLC (57) ABSTRACT

A fuel production plant includes an electrolysis apparatus; an ethanol generation apparatus that decomposes sugars to generate ethanol and carbon dioxide; and a hydrocarbon generation apparatus that generates hydrocarbons by reacting carbon dioxide with hydrogen. The fuel production plant further includes a hydrogen supply part that supplies hydrogen generated in the electrolysis apparatus to the hydrocarbon generation apparatus by coupling the electrolysis apparatus to the hydrocarbon generation apparatus, an oxygen supply part that supplies oxygen generated in the electrolysis apparatus to the ethanol generation apparatus by coupling the electrolysis apparatus to the ethanol generation apparatus, and a carbon dioxide supply part that supplies carbon dioxide generated in the ethanol generation apparatus to the hydrocarbon generation apparatus by coupling the ethanol generation apparatus to the hydrocarbon generation apparatus.

6 Claims, 5 Drawing Sheets

(51) Int. Cl.
   *C12P 7/06*    (2006.01)
   *C07C 1/12*    (2006.01)

(52) U.S. Cl.
   CPC ... *C10L 2200/0461* (2013.01); *C10L 2290/26* (2013.01); *C10L 2290/58* (2013.01)

(56) References Cited

U.S. PATENT DOCUMENTS

| | | | |
|---|---|---|---|
| 2013/0149755 A1* | 6/2013 | Reed | C12P 7/6463 |
| | | | 204/278 |
| 2013/0331616 A1* | 12/2013 | Olah | C10G 3/42 |
| | | | 95/139 |
| 2014/0080076 A1* | 3/2014 | Lutz | F23L 7/007 |
| | | | 431/253 |
| 2016/0230311 A1* | 8/2016 | Vince | C25B 1/04 |
| 2017/0218404 A1* | 8/2017 | Simpson | C25B 1/23 |
| 2017/0240936 A1* | 8/2017 | Smith | C12M 29/00 |
| 2018/0086985 A1* | 3/2018 | von Olshausen | B01D 53/047 |
| 2018/0245108 A1* | 8/2018 | Reed | C12M 29/20 |
| 2019/0185887 A1* | 6/2019 | Foody | C01B 3/16 |
| 2019/0210872 A1* | 7/2019 | Lewis | B01D 53/73 |
| 2020/0010771 A1* | 1/2020 | Yoon | B01D 53/268 |
| 2021/0285127 A1* | 9/2021 | Vince | C30B 35/007 |
| 2021/0324301 A1* | 10/2021 | Lorén | C11C 3/003 |
| 2021/0340075 A1* | 11/2021 | Schuetzle | B01J 23/005 |
| 2022/0251455 A1* | 8/2022 | Schuetzle | B01J 23/02 |
| 2022/0267810 A1* | 8/2022 | Lyubovsky | C07C 1/12 |
| 2022/0325227 A1* | 10/2022 | Conrado | C12M 43/04 |

\* cited by examiner

FUEL PRODUCTION PLANT

CROSS REFERENCE TO RELATED APPLICATIONS

This application is based upon and claims the benefit of priority from Japanese patent application No. 2021-124130, filed on Jul. 29, 2021, the disclosure of which is incorporated herein in its entirety by reference.

BACKGROUND

The present disclosure relates to a fuel production plant.

Patent Literature 1 (Japanese Unexamined Patent Application Publication No. 2013-202044) discloses a technique for generating methane using bioethanol-derived hydrogen and carbon dioxide.

Patent Literature 2 (Japanese Unexamined Patent Application Publication No. 2021-102532) proposes using oxygen, which is a by-product produced when water is electrolyzed, to generate carbon dioxide used when ammonia derivatives are synthesized, in order to efficiently use this oxygen.

SUMMARY

There is a room for improving the cost for generating hydrocarbons by reacting carbon dioxide with hydrogen.

An object of the present disclosure is to provide a technique for reducing the cost for generating hydrocarbons by reacting carbon dioxide with hydrogen.

According to an aspect of the present disclosure, a fuel production plant including: an electrolysis apparatus configured to electrolyze water to generate hydrogen and oxygen; an ethanol generation apparatus configured to decompose sugars to generate ethanol and carbon dioxide; a hydrocarbon generation apparatus configured to generate hydrocarbons by reacting carbon dioxide with hydrogen; a hydrogen supply part configured to supply hydrogen generated in the electrolysis apparatus to the hydrocarbon generation apparatus by coupling the electrolysis apparatus to the hydrocarbon generation apparatus; an oxygen supply part configured to supply oxygen generated in the electrolysis apparatus to the ethanol generation apparatus by coupling the electrolysis apparatus to the ethanol generation apparatus; and a carbon dioxide supply part configured to supply carbon dioxide generated in the ethanol generation apparatus to the hydrocarbon generation apparatus by coupling the ethanol generation apparatus to the hydrocarbon generation apparatus is provided.

The ethanol generation apparatus may include at least one of: a yeast fungus producing part configured to produce yeast fungus; a saccharifying enzyme producing part configured to produce saccharifying enzyme; and a boiler, and oxygen supplied to the ethanol generation apparatus by the oxygen supply part may be consumed in at least one of the yeast fungus producing part, the saccharifying enzyme producing part, and the boiler.

The ethanol generation apparatus may include a fermentation part that decomposes monosaccharides or oligosaccharides using yeast fungus, and the carbon dioxide supply part may supply exhaust gas from the fermentation part to the hydrocarbon generation apparatus when a predetermined amount of time has passed after the ethanol generation apparatus is put into operation or the concentration of carbon dioxide in the exhaust gas from the fermentation part becomes equal to or larger than a first threshold.

The carbon dioxide supply part may release the exhaust gas from the fermentation part into the atmosphere until a predetermined amount of time has passed since the ethanol generation apparatus is put into operation or as long as the concentration of carbon dioxide in the exhaust gas from the fermentation part remains smaller than the first threshold.

The carbon dioxide supply part may concentrate the exhaust gas from the fermentation part in such a way that the concentration of carbon dioxide in this exhaust gas increases, and supply the exhaust gas after the concentration thereof to the hydrocarbon generation apparatus until a predetermined amount of time has passed since the ethanol generation apparatus is put into operation or as long as the concentration of carbon dioxide in the exhaust gas from the fermentation part remains smaller than the first threshold.

The fuel production plant may further include an algae growing apparatus configured to grow algae or an organic acid synthesis apparatus configured to reduce carbon dioxide and synthesize organic acids, in which the carbon dioxide supply part may supply the exhaust gas from the fermentation part to the algae growing apparatus or the organic acid synthesis apparatus until a predetermined amount of time has passed since the ethanol generation apparatus is put into operation or as long as the concentration of carbon dioxide in the exhaust gas from the fermentation part remains smaller than the first threshold.

The carbon dioxide supply part may include a carbon dioxide storage part in which carbon dioxide generated in the ethanol generation apparatus is stored, and supply the carbon dioxide stored in the carbon dioxide storage part to the hydrocarbon generation apparatus.

A carbon dioxide recovery apparatus configured to recover carbon dioxide from the atmosphere and supply the recovered carbon dioxide to the carbon dioxide storage part; and a controller that is configured to operate the carbon dioxide recovery apparatus in such a way that the volume of carbon dioxide stored in the carbon dioxide storage part increases when this storage volume is below a predetermined value may be further included.

According to the present disclosure, the cost for generating hydrocarbons by reacting carbon dioxide with hydrogen is reduced.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF EMBODIMENTS

Figure 1:
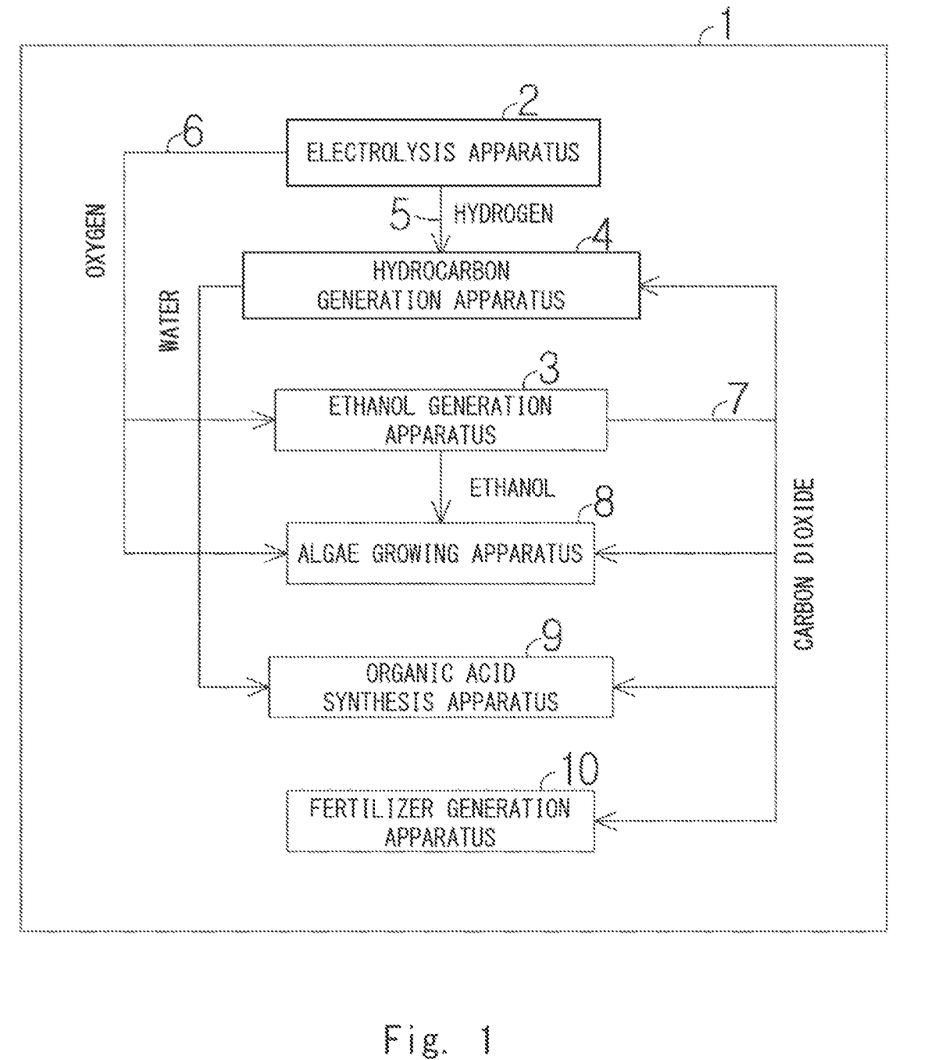
FIG. 1 is a schematic configuration diagram of a fuel production plant.

Hereinafter, with reference to FIGS. 1 to 5, a preferable embodiment of the present disclosure will be described. FIG. 1 shows a fuel production plant 1 according to this embodiment.

The fuel production plant 1 at least includes an electrolysis apparatus 2, an ethanol generation apparatus 3, a hydrocarbon generation apparatus 4, a hydrogen supply part 5, an oxygen supply part 6, and a carbon dioxide supply part 7.

The electrolysis apparatus 2 electrolyzes water to generate hydrogen and oxygen.

The ethanol generation apparatus 3 decomposes sugars to generate ethanol and carbon dioxide.

The hydrocarbon generation apparatus 4 generates hydrocarbons by reacting carbon dioxide with hydrogen.

The hydrogen supply part 5 supplies hydrogen generated in the electrolysis apparatus 2 to the hydrocarbon generation apparatus 4 by coupling the electrolysis apparatus 2 to the hydrocarbon generation apparatus 4 by using, for example, a pipe.

The oxygen supply part 6 supplies oxygen generated in the electrolysis apparatus 2 to the ethanol generation apparatus 3 by coupling the electrolysis apparatus 2 to the ethanol generation apparatus 3 by using, for example, a pipe.

The carbon dioxide supply part 7 supplies carbon dioxide generated in the ethanol generation apparatus 3 to the hydrocarbon generation apparatus 4 by coupling the ethanol generation apparatus 3 to the hydrocarbon generation apparatus 4 by using, for example, a pipe.

According to the above configuration, it is possible to efficiently use oxygen generated in the electrolysis apparatus 2 as a by-product, and carbon dioxide generated in the ethanol generation apparatus 3 as a by-product, whereby hydrocarbons can be generated in the hydrocarbon generation apparatus 4 at a low cost.

As shown in FIG. 1, the fuel production plant 1 further includes an algae growing apparatus 8, an organic acid synthesis apparatus 9, and a fertilizer generation apparatus 10.

The algae growing apparatus 8 is configured in such a way that carbon dioxide generated in the ethanol generation apparatus 3 is supplied to the algae growing apparatus 8 via the carbon dioxide supply part 7. The algae growing apparatus 8 is configured in such a way that ethanol generated in the ethanol generation apparatus 3 is supplied to the algae growing apparatus 8. The algae growing apparatus 8 is further configured in such a way that oxygen generated in the electrolysis apparatus 2 is supplied to the algae growing apparatus 8 via the oxygen supply part 6.

The organic acid synthesis apparatus 9 is configured in such a way that carbon dioxide generated in the ethanol generation apparatus 3 is supplied to the organic acid synthesis apparatus 9 via the carbon dioxide supply part 7. The organic acid synthesis apparatus 9 is configured in such a way that water, which is a by-product generated in the hydrocarbon generation apparatus 4, is supplied to the organic acid synthesis apparatus 9.

The fertilizer generation apparatus 10 is configured in such a way that carbon dioxide generated in the ethanol generation apparatus 3 is supplied to the fertilizer generation apparatus 10 via the carbon dioxide supply part 7.

The algae growing apparatus 8 is, for example, an apparatus that grows algae such as Asparagopsis taxiformis or *Euglena*. It is expected that Asparagopsis taxiformis will be able to eliminate cow burps. *Euglena* may be used as a raw material for jet fuel and diesel fuel. The algae growing apparatus 8 promotes the growth of algae using carbon dioxide supplied from the ethanol generation apparatus 3. Further, the algae growing apparatus 8 may use ethanol supplied from the ethanol generation apparatus 3 as a nutrient source for cultivating algae. Further, the algae growing apparatus 8 may promote growth of fish using oxygen supplied from the electrolysis apparatus 2. It is considered that fish contribute to the growth of algae since their excretions provide nutrients to algae during its growth. Further, it may be possible for the algae growing apparatus 8 to utilize iron and steel slag exhausted from steel mills for growing algae. It is expected that the iron and steel slag will contribute to proliferation of algae since it includes a large amount of iron, phosphorus, magnesium, calcium, and manganese.

The organic acid synthesis apparatus 9 reduces carbon dioxide and synthesizes organic acids. Organic acids are typically acetic acid or formic acid. It is expected that organic acids, when mixed with silage, will cause the activity of microorganisms contained in the silage to be reduced, thereby inhibiting over-fermentation that causes deterioration in flavor of the silage. It is further expected that organic acids will temporarily inhibit the activity of yeast fungus in the ethanol generation apparatus 3, thereby increasing the subsequent activity of yeast fungus. Therefore, organic acids generated in the organic acid synthesis apparatus 9 may be configured to be supplied to the ethanol generation apparatus 3.

The fertilizer generation apparatus 10 generates ammonia and urea by reacting carbon dioxide supplied from the ethanol generation apparatus 3 with nitrogen separated from the atmosphere. Ammonia and urea may be used as fertilizer.

Figure 2:
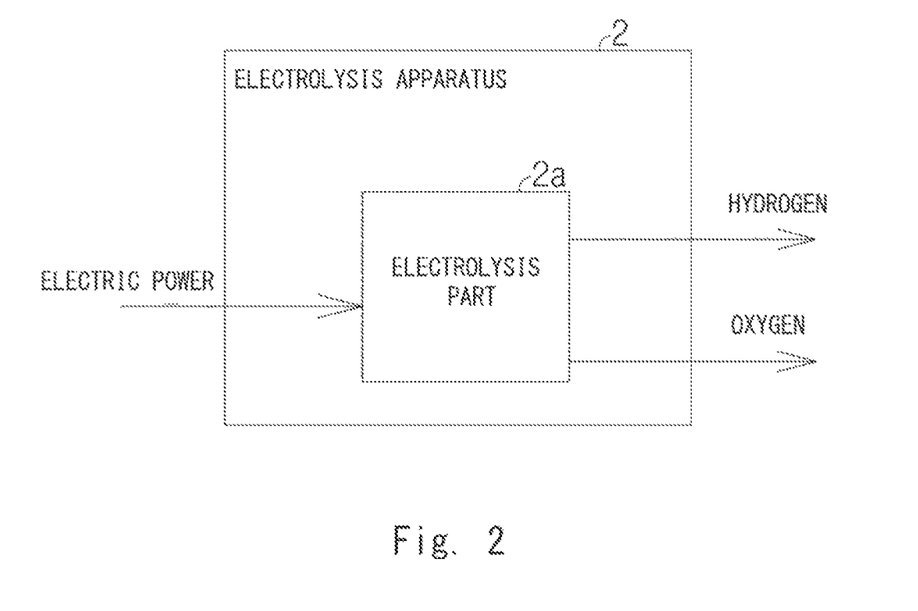
FIG. 2 is a configuration diagram of an electrolysis apparatus.

FIG. 2 shows a configuration diagram of the electrolysis apparatus 2. As shown in FIG. 2, the electrolysis apparatus 2 includes an electrolysis part 2a that electrolyzes water to generate hydrogen and oxygen using, for example, electric power supplied from an external power source such as solar panels.

Figure 3:
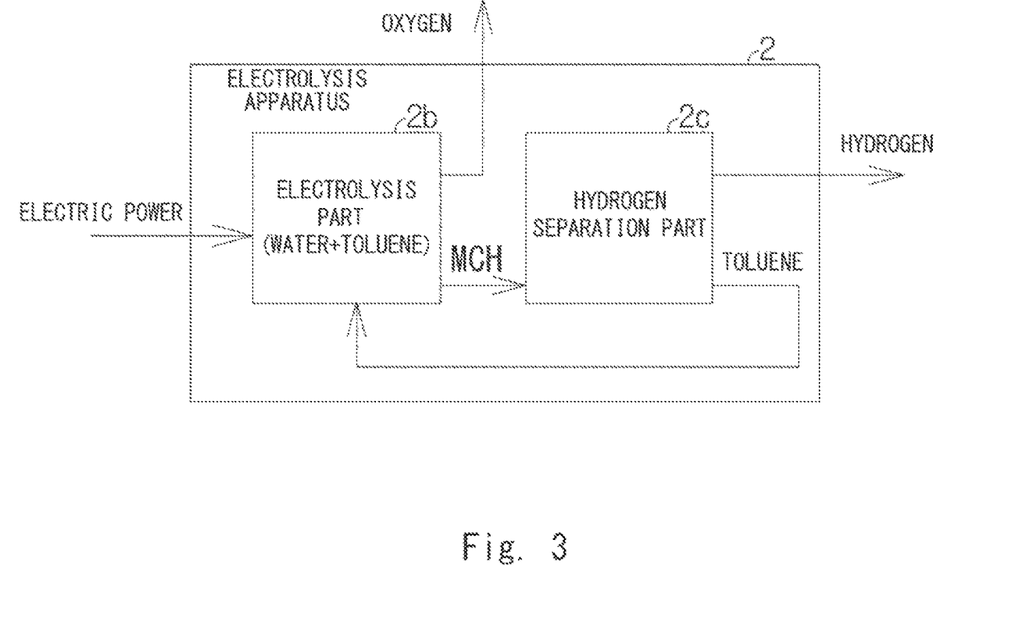
FIG. 3 is a configuration diagram of the electrolysis apparatus.

FIG. 3 shows a modified example of the electrolysis apparatus 2. As shown in FIG. 3, in this modified example, the electrolysis apparatus 2 includes an electrolysis part 2b and a hydrogen separation part 2c. The electrolysis part 2b generates methylcyclohexane (MCH) and oxygen using an organic hydride electrolytic synthesis method. The hydrogen separation part 2c separates hydrogen from methylcyclohexane generated in the electrolysis part 2b. Since methylcyclohexane is liquid at room temperature, it is suitable for being stored and transported, and hydrogen can be easily separated from methylcyclohexane. It is thus possible to store methylcyclohexane generated in the electrolysis apparatus 2 and carry it out of the fuel production plant 1.

Referring once again to FIG. 1, the hydrocarbon generation apparatus 4 generates hydrocarbons by reacting carbon dioxide with hydrogen. Specifically, the hydrocarbon generation apparatus 4 generates hydrocarbons in accordance with the following reaction formula.

$$nCO_2+(3n+1)H_2 \rightarrow CnH_{2n+2}+2nH_2O$$

Hydrocarbons, which are typically methane, are rectified to liquefied methane, which can be used for many purposes as a synthetic liquid fuel. Further, if the final product is isoparaffin with about 5 to 13 carbon atoms, hydrocarbons can be used as a fuel that is further suitable for transportation.

Water, which is a by-product produced in the hydrocarbon generation apparatus 4, may be used in the electrolysis apparatus 2. Alternatively, water may be used to grow fish in the algae growing apparatus 8 or may be used in the fermentation part 22 of the ethanol generation apparatus 3.

Figure 4:
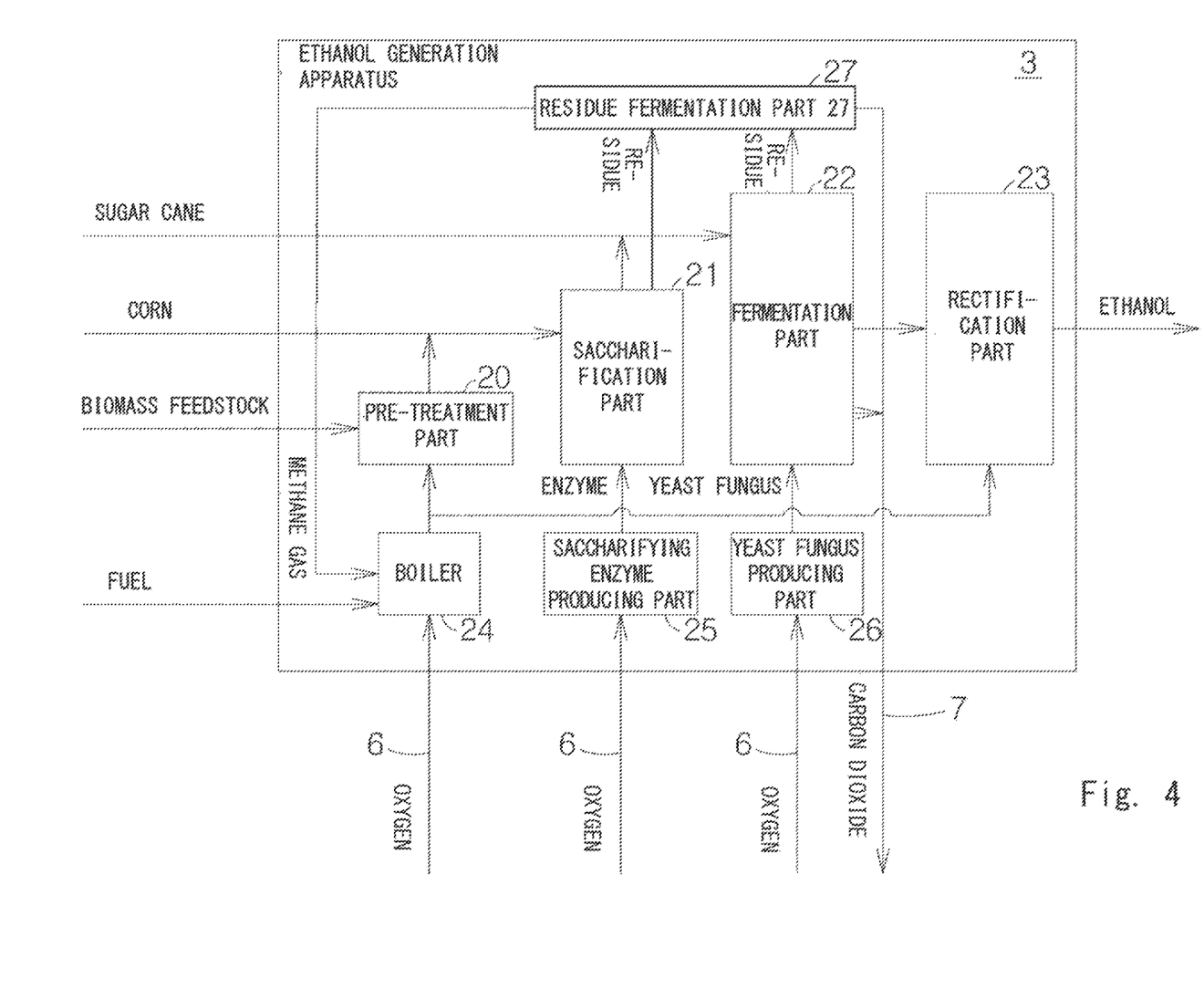
FIG. 4 is a configuration diagram of an ethanol generation apparatus.

FIG. 4 shows a configuration diagram of the ethanol generation apparatus 3. The ethanol generation apparatus 3 includes a pre-treatment part 20, a saccharification part 21, a fermentation part 22, a rectification part 23, a boiler 24, a saccharifying enzyme producing part 25, a yeast fungus producing part 26, and a residue fermentation part 27.

The pre-treatment part 20 separates cellulose, which polysaccharides, from a biomass feedstock externally supplied.

The saccharification part 21 decomposes polysaccharides supplied from the pre-treatment part 20 or externally supplied into monosaccharides or oligosaccharides using saccharifying enzyme. Polysaccharides that are externally supplied are typically corn.

The fermentation part 22 decomposes monosaccharides or oligosaccharides supplied from the saccharification part 21 or externally supplied using yeast fungus to generate ethanol and carbon dioxide. The oligosaccharides externally supplied are typically sugar cane. The fermentation part 22 may be configured as a continuous type in which the above decomposition process is performed continuously, or as a batch type in which the above decomposition process is performed intermittently. The fermentation part 22 discharges the generated carbon dioxide into the carbon dioxide supply part 7. The fermentation part 22 supplies the generated ethanol to the rectification part 23.

The rectification part 23 rectifies ethanol supplied from the fermentation part 22. Ethanol rectified by the rectification part 23 is typically used for various purposes as a so-called bioethanol.

The boiler 24 burns fuel externally supplied and the fuel (methane gas) supplied from the residue fermentation part 27 and generates steam using the heat of combustion obtained during combustion. The steam generated in the boiler 24 is supplied to the pre-treatment part 20 and is used as a heat source in the process of separating the biomass feedstock in the pre-treatment part 20. Further, the steam generated in the boiler 24 is supplied to the rectification part 23 and is used as a heat source in the rectification process in the boiler 24. The boiler 24 is supplied with oxygen via the oxygen supply part 6, and this oxygen is used to burn the fuel. This supply of oxygen allows the power consumption of the blower that pressure-feeds air to the boiler 24 to be reduced. The boiler 24 may be of an electrical heating type, not a combustion type. Alternatively, a steam turbine may be connected to the boiler 24 and power may be generated using the steam generated in the boiler 24.

The saccharifying enzyme producing part 25 produces saccharifying enzyme. The saccharifying enzyme producing part 25 supplies the produced saccharifying enzyme to the saccharification part 21. The saccharifying enzyme producing part 25 is supplied with oxygen via the oxygen supply part 6, and this oxygen is used to produce saccharifying enzyme. This supply of oxygen allows the power consumption of the blower that pressure-feeds air to the saccharifying enzyme producing part 25 to be reduced.

The yeast fungus producing part 26 produces yeast fungus. The yeast fungus producing part 26 supplies the produced yeast fungus to the fermentation part 22. The yeast fungus producing part 26 is supplied with oxygen via the oxygen supply part 6 and this oxygen is used to produce yeast fungus. This supply of oxygen allows the power consumption in the blower that pressure-feeds air to the yeast fungus producing part 26 to be reduced.

The residue fermentation part 27 generates methane gas and carbon dioxide through methane fermentation of the residue exhausted from the saccharification part 21 and the fermentation part 22. The residue fermentation part 27 supplies the generated methane gas to the boiler 24. Further, the residue fermentation part 27 discharges the generated carbon dioxide into the carbon dioxide supply part 7.

Figure 5:
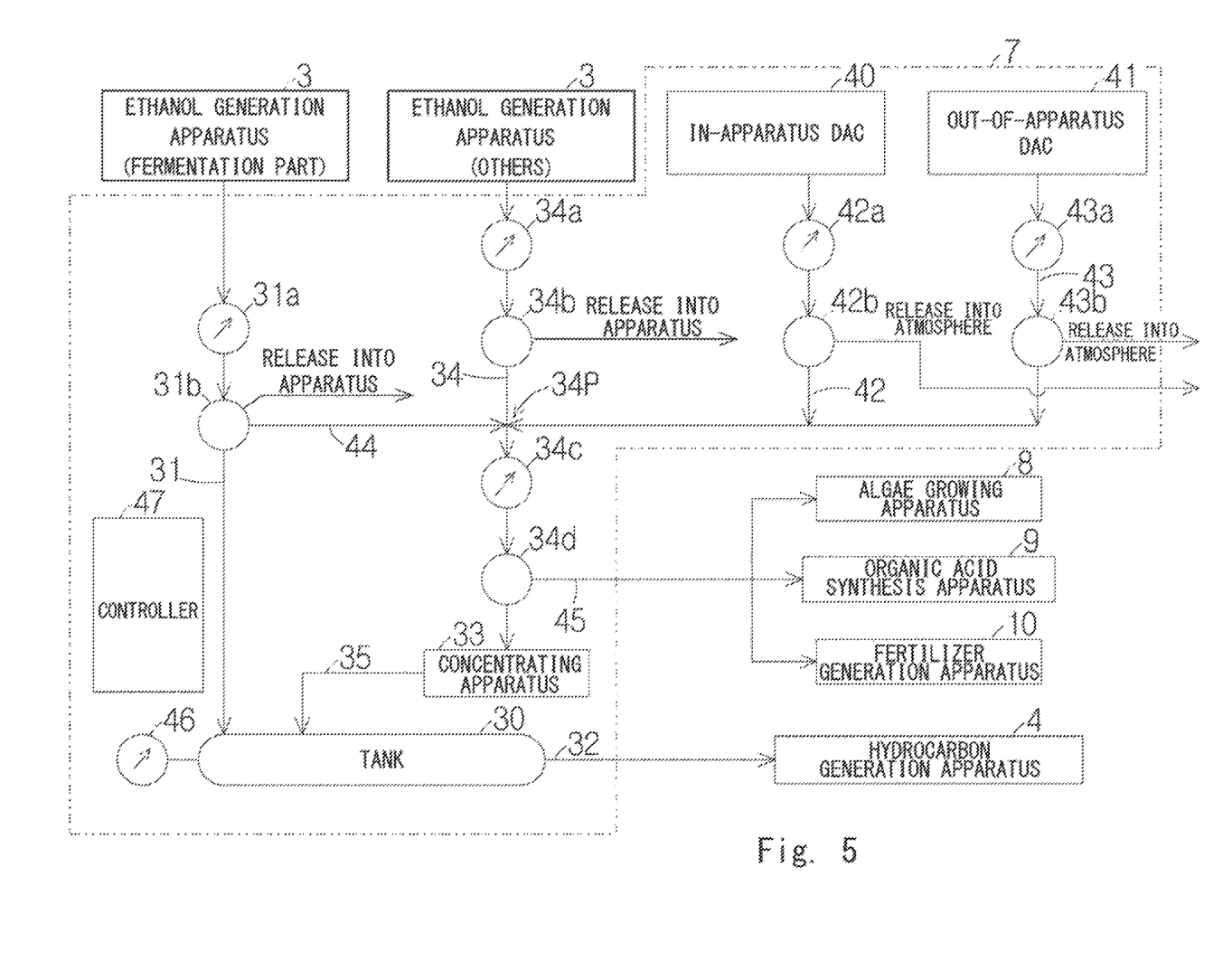
FIG. 5 is a configuration diagram of a carbon dioxide supply part.

FIG. 5 shows a configuration diagram of the carbon dioxide supply part 7. As described above, the carbon dioxide supply part 7 supplies carbon dioxide generated in the ethanol generation apparatus 3 to the hydrocarbon generation apparatus 4 by coupling the ethanol generation apparatus 3 to the hydrocarbon generation apparatus 4. However, the concentration of carbon dioxide in the exhaust gas exhausted from the ethanol generation apparatus 3 is not constant. For example, the concentration of carbon dioxide in the exhaust gas immediately after the operation of the ethanol generation apparatus 3 is started is low. Further, even after a predetermined amount of time has passed since the ethanol generation apparatus 3 is put into operation, the concentration of carbon dioxide in the exhaust gas may be temporarily reduced. Therefore, as shown in FIG. 5, the carbon dioxide supply part 7 includes various configurations in order to stably supply carbon dioxide to the hydrocarbon generation apparatus 4.

That is, the carbon dioxide supply part 7 includes a tank 30, which is a carbon dioxide storage part that stores carbon dioxide generated in the ethanol generation apparatus 3. The carbon dioxide supply part 7 stores carbon dioxide generated in the ethanol generation apparatus 3 in the tank 30 and supplies carbon dioxide stored in the tank 30 to the hydrocarbon generation apparatus 4. Accordingly, even when the concentration of carbon dioxide in the exhaust gas exhausted from the ethanol generation apparatus 3 is temporarily reduced, carbon dioxide can be stably supplied to the hydrocarbon generation apparatus 4.

Specifically, the carbon dioxide supply part 7 includes a first pipe 31 that couples the ethanol generation apparatus 3 to the tank 30, and a second pipe 32 that couples the tank 30 to the hydrocarbon generation apparatus 4. The first pipe 31 is connected to the fermentation part 22 of the ethanol generation apparatus 3. Therefore, exhaust gas with a high concentration of carbon dioxide mainly flows through the first pipe 31. A first concentration meter 31$a$ and a first switching valve 31$b$ are provided in the first pipe 31 in this order along the direction of the flow of the exhaust gas.

The carbon dioxide supply part 7 includes a concentrating apparatus 33. The carbon dioxide supply part 7 includes a third pipe 34 that couples the ethanol generation apparatus 3 to the concentrating apparatus 33, and a fourth pipe 35 that couples the concentrating apparatus 33 to the tank 30. The third pipe 34 is connected to the pre-treatment part 20, the saccharification part 21, the rectification part 23, the saccharifying enzyme producing part 25, the yeast fungus producing part 26, and the residue fermentation part 27 of the ethanol generation apparatus 3. Therefore, exhaust gas with a moderate concentration of carbon dioxide mainly flows through the third pipe 34. A second concentration meter 34$a$, a second switching valve 34$b$, a third concentration meter 34$c$, and a third switching valve 34$d$ are provided in this order in the third pipe 34 along the direction of the flow of the exhaust gas.

The carbon dioxide supply part 7 includes an in-apparatus Direct Air Capture (DAC) 40 and an out-of-apparatus DAC 41. The in-apparatus DAC 40 captures carbon dioxide from the air in the ethanol generation apparatus 3 that forms a closed space using, for example, an amine absorption process. The out-of-apparatus DAC 41 captures carbon dioxide from the air outside the ethanol generation apparatus 3. The carbon dioxide supply part 7 includes a fifth pipe 42 that couples the in-apparatus DAC 40 to the third pipe 34 and a sixth pipe 43 that couples the out-of-apparatus DAC 41 to the third pipe 34.

The fifth pipe 42 is connected to a junction 34P which is between the second switching valve 34b and the third concentration meter 34c of the third pipe 34. Likewise, the sixth pipe 43 is connected to the junction 34P.

A fourth concentration meter 42a and a fourth switching valve 42b are provided in this order in the fifth pipe 42 along the direction of the flow of the exhaust gas. Likewise, a fifth concentration meter 43a and a fifth switching valve 43b are provided in this order in the sixth pipe 43 along the direction of the flow of the exhaust gas.

The carbon dioxide supply part 7 further includes a seventh pipe 44 that couples the first switching valve 31b to the third pipe 34. The seventh pipe 44 is connected to the junction 34P.

Further, the carbon dioxide supply part 7 includes an eighth pipe 45 that couples the third switching valve 34d to the algae growing apparatus 8, the organic acid synthesis apparatus 9, and the fertilizer generation apparatus 10.

Further, the carbon dioxide supply part 7 includes a storage volume sensor 46 that measures the amount of carbon dioxide stored in the tank 30, and a controller 47.

The storage volume sensor 46 typically measures the internal pressure value of the tank 30.

The controller 47 receives output signals from the first concentration meter 31a, the second concentration meter 34a, the third concentration meter 34c, the fourth concentration meter 42a, the fifth concentration meter 43a, and the storage volume sensor 46. The controller 47 controls operations of the first switching valve 31b, the second switching valve 34b, the third switching valve 34d, the fourth switching valve 42b, the fifth switching valve 43b, the in-apparatus DAC 40, the out-of-apparatus DAC 41, and the concentrating apparatus 33 based on the results of the reception. The controller 47, which is typically a computer that includes a CPU, a RAM, and a ROM, executes the aforementioned control by a CPU loading the program stored in the ROM and executing the loaded program.

Next, operations of the carbon dioxide supply part 7 will be described in detail.

First, when the operation of the ethanol generation apparatus 3 is started, exhaust gas including carbon dioxide is exhausted from the ethanol generation apparatus 3. The concentration of carbon dioxide in the exhaust gas from the ethanol generation apparatus 3 immediately after the ethanol generation apparatus 3 starts operation is substantially the same as that in the ambient air, and is gradually increased with time.

The controller 47 acquires the concentration of carbon dioxide of the exhaust gas exhausted from the ethanol generation apparatus 3 to the first pipe 31 based on an output signal of the first concentration meter 31a. When the concentration of carbon dioxide of the exhaust gas is smaller than the low-concentration side threshold, the controller 47 controls the first switching valve 31b to release this exhaust gas into the ethanol generation apparatus 3. When the concentration of carbon dioxide of the exhaust gas is smaller than the low-concentration side threshold, the controller 47 may control the first switching valve 31b to release this exhaust gas into the atmosphere outside the ethanol generation apparatus 3. When the concentration of carbon dioxide of the exhaust gas is equal to or larger than the low-concentration side threshold but is smaller than the high-concentration side threshold, the controller 47 controls the first switching valve 31b in such a way that this exhaust gas flows through the seventh pipe 44. When the concentration of carbon dioxide of the exhaust gas is equal to or higher than the high-concentration side threshold, the controller 47 controls the first switching valve 31b in such a way that this exhaust gas flows toward the tank 30. According to this control, it is possible to prevent exhaust gas whose concentration of carbon dioxide is low from being supplied to the tank 30. The low-concentration side threshold is, for example, but not limited to, 0.3 to 0.5 vol % and the high-concentration side threshold is, for example, but not limited to, 95 to 98 vol %.

The controller 47 acquires the concentration of carbon dioxide of the exhaust gas exhausted from the ethanol generation apparatus 3 to the third pipe 34 based on an output signal of the second concentration meter 34a. When the concentration of carbon dioxide of the exhaust gas is smaller than the low-concentration side threshold, the controller 47 controls the second switching valve 34b to release this exhaust gas into the ethanol generation apparatus 3. When the concentration of carbon dioxide of the exhaust gas is smaller than the low-concentration side threshold, the controller 47 may control the second switching valve 34b to release this exhaust gas into the atmosphere outside the ethanol generation apparatus 3. When the concentration of carbon dioxide of the exhaust gas is equal to or larger than the low-concentration side threshold, the controller 47 controls the second switching valve 34b in such a way that this exhaust gas flows toward the junction 34P.

The controller 47 acquires the concentration of carbon dioxide of the gas that is supplied to the fifth pipe 42 from the in-apparatus DAC 40 based on an output signal of the fourth concentration meter 42a. When the concentration of carbon dioxide of the gas is smaller than the low-concentration side threshold, the controller 47 controls the fourth switching valve 42b to release this gas into the atmosphere outside the ethanol generation apparatus 3. When the concentration of carbon dioxide of the gas is equal to or larger than the low-concentration side threshold, the controller 47 controls the fourth switching valve 42b in such a way that this gas flows toward the junction 34P.

The controller 47 acquires the concentration of carbon dioxide of the gas that is supplied to the sixth pipe 43 from the out-of-apparatus DAC 41 based on an output signal of the fifth concentration meter 43a. When the concentration of carbon dioxide of the gas is smaller than the low-concentration side threshold, the controller 47 controls the fifth switching valve 43b to release this gas into the atmosphere outside the ethanol generation apparatus 3. When the concentration of carbon dioxide of the gas is equal to or larger than the low-concentration side threshold, the controller 47 controls the fifth switching valve 43b in such a manner that this gas flows toward the junction 34P.

The controller 47 acquires the concentration of carbon dioxide of the gas that flows downstream from the junction 34P based on an output signal of the third concentration meter 34c. When the concentration of carbon dioxide of the gas is smaller than a middle-concentration side threshold, the controller 47 controls the third switching valve 34d to supply this gas to one or more of the algae growing apparatus 8, the organic acid synthesis apparatus 9, or the fertilizer generation apparatus 10. When the concentration of carbon dioxide of the gas is equal to or larger than the middle-concentration side threshold, the controller 47 controls the third switching valve 34d in such a way that this gas flows toward the concentrating apparatus 33. Note that the middle-concentration side threshold is, for example, but is not limited to, 10 vol %.

The concentrating apparatus 33 concentrates the gas supplied from the third pipe 34 in such a way that the concentration of carbon dioxide in this gas increases. Typically, the concentrating apparatus 33 concentrates the gas supplied from the third pipe 34 in such a way that the concentration of carbon dioxide in this gas becomes equal to or larger than the high-concentration side threshold. The method of concentration is typically a pressure swing (PSA) type adsorption method that uses a natural zeolite (ferrierite type). The concentrating apparatus 33 discharges the gas after being concentrated into the tank 30.

The gas supplied to the tank 30 is supplied to the hydrocarbon generation apparatus 4 via a gas compressor that is not shown.

The controller 47 acquires the internal pressure value of the tank 30 based on an output signal of the storage volume sensor 46. The controller 47 operates the in-apparatus DAC 40 and the out-of-apparatus DAC 41 when the internal pressure value is smaller than a predetermined value. It is therefore possible to recover the volume of carbon dioxide stored in the tank 30 (=the internal pressure value of the tank 30). When the internal pressure value is equal to or larger than the predetermined value, the controller 47 stops operating the in-apparatus DAC 40 and the out-of-apparatus DAC 41. Accordingly, the power consumption of the carbon dioxide supply part 7 can be reduced.

While the preferable embodiment has been described above, the above embodiment has the following features.

As shown in FIG. 1, the fuel production plant 1 includes the electrolysis apparatus 2 configured to electrolyze water to generate hydrogen and oxygen, the ethanol generation apparatus 3 configured to decompose sugars to generate ethanol and carbon dioxide, and the hydrocarbon generation apparatus 4 configured to generate hydrocarbons by reacting carbon dioxide with hydrogen. The fuel production plant 1 further includes the hydrogen supply part 5 configured to supply hydrogen generated in the electrolysis apparatus 2 to the hydrocarbon generation apparatus 4 by coupling the electrolysis apparatus 2 to the hydrocarbon generation apparatus 4, the oxygen supply part 6 configured to supply oxygen generated in the electrolysis apparatus 2 to the ethanol generation apparatus 3 by coupling the electrolysis apparatus 2 to the ethanol generation apparatus 3, and the carbon dioxide supply part 7 configured to supply carbon dioxide generated in the ethanol generation apparatus 3 to the hydrocarbon generation apparatus 4 by coupling the ethanol generation apparatus 3 to the hydrocarbon generation apparatus 4. According to the above configuration, it is possible to efficiently use oxygen generated in the electrolysis apparatus 2 as a by-product and carbon dioxide generated in the ethanol generation apparatus 3 as a by-product, whereby hydrocarbons can be generated in the hydrocarbon generation apparatus 4 at a low cost.

Further, as shown in FIG. 4, the ethanol generation apparatus 3 includes the yeast fungus production part 26 configured to produce yeast fungus, the saccharifying enzyme producing part 25 that produces saccharifying enzyme, and the boiler 24. Oxygen supplied to the ethanol generation apparatus 3 by the oxygen supply part 6 is consumed by the yeast fungus producing part 26, the saccharifying enzyme producing part 25, and the boiler 24. According to the above configuration, oxygen supplied to the ethanol generation apparatus 3 by the oxygen supply part 6 can be efficiently used. Note that one or more of the yeast fungus producing part 26, the saccharifying enzyme producing part 25, and the boiler 24 may be omitted. The oxygen supplied to the ethanol generation apparatus 3 by the oxygen supply part 6 may be used by at least one of the yeast fungus producing part 26, the saccharifying enzyme producing part 25, and the boiler 24.

As shown in FIG. 4, the ethanol generation apparatus 3 includes the fermentation part 22 that decomposes monosaccharides or oligosaccharides using yeast fungus. When the concentration of carbon dioxide in the exhaust gas from the fermentation part 22 becomes equal to or larger than the high-concentration side threshold (first threshold), the carbon dioxide supply part 7 supplies the exhaust gas from the fermentation part 22 to the hydrocarbon generation apparatus 4. According to the above configuration, it is possible to prevent gas whose concentration of carbon dioxide is low from being supplied to the hydrocarbon generation apparatus 4. Instead of monitoring the concentration of carbon dioxide in the exhaust gas from the fermentation part 22 and determining whether to supply the exhaust gas from the fermentation part 22 to the hydrocarbon generation apparatus 4 based on the results of the monitoring, the carbon dioxide supply part 7 may make the above determination based on a time elapsed since the start of the operation of the ethanol generation apparatus 3. After, for example, the time elapsed since the start of the operation of the ethanol generation apparatus 3 reaches eight hours, the exhaust gas from the fermentation part 22 may be supplied to the hydrocarbon generation apparatus 4. In this case, a concentration meter for measuring the concentration of carbon dioxide in the exhaust gas from the ethanol generation apparatus 3 may be omitted.

Further, the carbon dioxide supply part 7 may release the exhaust gas from the fermentation part 22 into the atmosphere as long as the concentration of carbon dioxide in the exhaust gas from the fermentation part 22 is smaller than the high-concentration side threshold. According to the above configuration, it is possible to prevent gas whose concentration of carbon dioxide is low from being supplied to the hydrocarbon generation apparatus 4.

Further, the carbon dioxide supply part 7 may concentrate the exhaust gas from the fermentation part 22 in such a way that the concentration of carbon dioxide in this exhaust gas increases and supply exhaust gas after the concentration thereof to the hydrocarbon generation apparatus 4 as long as the concentration of carbon dioxide in the exhaust gas from the fermentation part 22 is smaller than the high-concentration side threshold. According to the above configuration, it is possible to prevent gas whose concentration of carbon dioxide is low from being supplied to the hydrocarbon generation apparatus 4.

Further, the fuel production plant 1 further includes the algae growing apparatus 8 for growing algae and the organic acid synthesis apparatus 9 that reduces carbon dioxide to synthesize organic acids. The carbon dioxide supply part 7 may supply the exhaust gas from the fermentation part 22 to the algae growing apparatus 8 and the organic acid synthesis apparatus 9 as long as the concentration of carbon dioxide in the exhaust gas from the fermentation part 22 is smaller than the high-concentration side threshold. According to the above configuration, it is possible to efficiently use exhaust gas whose concentration of carbon dioxide is low.

Further, the carbon dioxide supply part 7 includes the tank 30 (carbon dioxide storage part) that stores carbon dioxide generated in the ethanol generation apparatus 3. Carbon dioxide generated in the ethanol generation apparatus 3 is stored in the tank 30 and carbon dioxide stored in the tank 30 is supplied to the hydrocarbon generation apparatus 4. According to the above configuration, carbon dioxide can be stably supplied to the hydrocarbon generation apparatus 4.

Further, the fuel production plant 1 includes the in-apparatus DAC 40 and the out-of-apparatus DAC 41, which are carbon dioxide recovery apparatuses that recover carbon dioxide from the atmosphere and supply the recovered carbon dioxide to the tank 30. The fuel production plant 1 further includes the controller 47 that operates the in-apparatus DAC 40 and the out-of-apparatus DAC 41 so that the volume of carbon dioxide stored in the tank 30 increases when this storage volume is below a predetermined value. According to the above configuration, carbon dioxide can be supplied to the hydrocarbon generation apparatus 4 further stably.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A fuel production plant, comprising:
    an electrolysis apparatus configured to electrolyze water to generate hydrogen and oxygen;
    an ethanol generation apparatus configured to decompose sugars to generate ethanol and carbon dioxide;
    a hydrocarbon generation apparatus configured to generate hydrocarbons by reacting carbon dioxide with hydrogen;
    a hydrogen supply part configured to supply hydrogen generated in the electrolysis apparatus to the hydrocarbon generation apparatus by coupling the electrolysis apparatus to the hydrocarbon generation apparatus;
    an oxygen supply part configured to supply oxygen generated in the electrolysis apparatus to the ethanol generation apparatus by coupling the electrolysis apparatus to the ethanol generation apparatus;
    a carbon dioxide supply part configured to supply carbon dioxide generated in the ethanol generation apparatus to the hydrocarbon generation apparatus by coupling the ethanol generation apparatus to the hydrocarbon generation apparatus, wherein the carbon dioxide supply part includes a carbon dioxide storage part in which carbon dioxide generated in the ethanol generation apparatus is stored, and supplies the carbon dioxide stored in the carbon dioxide storage part to the hydrocarbon generation apparatus;
    a carbon dioxide recovery apparatus configured to recover carbon dioxide from the atmosphere and supply the recovered carbon dioxide to the carbon dioxide storage part; and
    a controller that is configured to operate the carbon dioxide recovery apparatus in such a way that the volume of carbon dioxide stored in the carbon dioxide storage part increases when this storage volume is below a predetermined value.

2. The fuel production plant according to claim 1, wherein the ethanol generation apparatus comprises at least one of:
    a yeast fungus producing part configured to produce yeast fungus;
    a saccharifying enzyme producing part configured to produce saccharifying enzyme; and
    a boiler, and
    oxygen supplied to the ethanol generation apparatus by the oxygen supply part is consumed in at least one of the yeast fungus producing part, the saccharifying enzyme producing part, and the boiler.

3. The fuel production plant according to claim 1, wherein the ethanol generation apparatus includes a fermentation part that decomposes monosaccharides or oligosaccharides using yeast fungus, and
    the carbon dioxide supply part supplies exhaust gas from the fermentation part to the hydrocarbon generation apparatus when a predetermined amount of time has passed after the ethanol generation apparatus is put into operation or the concentration of carbon dioxide in the exhaust gas from the fermentation part becomes equal to or larger than a first threshold.

4. The fuel production plant according to claim 3, wherein the carbon dioxide supply part releases the exhaust gas from the fermentation part into the atmosphere until a predetermined amount of time has passed since the ethanol generation apparatus is put into operation or as long as the concentration of carbon dioxide in the exhaust gas from the fermentation part remains smaller than the first threshold.

5. The fuel production plant according to claim 3, wherein the carbon dioxide supply part concentrates the exhaust gas from the fermentation part in such a way that the concentration of carbon dioxide in this exhaust gas increases, and supplies the exhaust gas after the concentration thereof to the hydrocarbon generation apparatus until a predetermined amount of time has passed since the ethanol generation apparatus is put into operation or as long as the concentration of carbon dioxide in the exhaust gas from the fermentation part remains smaller than the first threshold.

6. The fuel production plant according to claim 3, further comprising an algae growing apparatus configured to grow algae or an organic acid synthesis apparatus configured to reduce carbon dioxide and synthesize organic acids,
    wherein the carbon dioxide supply part supplies the exhaust gas from the fermentation part to the algae growing apparatus or the organic acid synthesis apparatus until a predetermined amount of time has passed since the ethanol generation apparatus is put into operation or as long as the concentration of carbon dioxide in the exhaust gas from the fermentation part remains smaller than the first threshold.

* * * * *